(12) United States Patent
Aqad (10) Patent No.: US 10,088,749 B2
(45) Date of Patent: Oct. 2, 2018

(54) PHOTOACID-GENERATING COMPOUND AND ASSOCIATED POLYMER, PHOTORESIST COMPOSITION, AND METHOD OF FORMING A PHOTORESIST RELIEF IMAGE

(71) Applicant: Rohm and Haas Electronic Materials LLC, Marlborough, MA (US)

(72) Inventor: Emad Aqad, Northborough, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 15/281,292

(22) Filed: Sep. 30, 2016

(65) Prior Publication Data
US 2018/0095363 A1    Apr. 5, 2018

(51) Int. Cl.
| | |
|---|---|
| G03F 7/004 | (2006.01) |
| G03F 7/30 | (2006.01) |
| C08F 228/02 | (2006.01) |
| C08F 228/06 | (2006.01) |
| C07D 333/74 | (2006.01) |
| C07C 309/02 | (2006.01) |
| C07C 309/06 | (2006.01) |
| C07C 309/12 | (2006.01) |
| C07C 309/14 | (2006.01) |
| C07C 309/22 | (2006.01) |
| C07C 309/23 | (2006.01) |
| C07C 309/19 | (2006.01) |
| C08F 220/68 | (2006.01) |
| G03F 7/039 | (2006.01) |
| G03F 7/16 | (2006.01) |
| G03F 7/20 | (2006.01) |
| G03F 7/32 | (2006.01) |
| G03F 7/40 | (2006.01) |
| C07C 303/32 | (2006.01) |
| C07C 309/04 | (2006.01) |

(52) U.S. Cl.
CPC .......... *G03F 7/0045* (2013.01); *C07C 303/32* (2013.01); *C07C 309/04* (2013.01); *C07C 309/06* (2013.01); *C07C 309/12* (2013.01); *C07C 309/14* (2013.01); *C07C 309/19* (2013.01); *C07C 309/22* (2013.01); *C07C 309/23* (2013.01); *C07D 333/74* (2013.01); *C08F 220/68* (2013.01); *C08F 228/02* (2013.01); *C08F 228/06* (2013.01); *G03F 7/0397* (2013.01); *G03F 7/16* (2013.01); *G03F 7/2004* (2013.01); *G03F 7/30* (2013.01); *G03F 7/322* (2013.01); *G03F 7/40* (2013.01)

(58) Field of Classification Search
CPC ....... G03F 7/0045; G03F 7/30; C07C 333/74; C08F 228/02; C08F 228/06

USPC ......... 430/270.1, 921, 922, 326; 549/12, 41, 549/42, 43, 45, 46, 47; 526/256, 280, 526/287, 288

See application file for complete search history.

(56) References Cited

U.S. PATENT DOCUMENTS

| | | | |
|---|---|---|---|
| 2,760,863 | A | 8/1956 | Plambeck, Jr. |
| 2,850,445 | A | 9/1958 | Oster |
| 2,875,047 | A | 2/1959 | Oster |
| 3,097,096 | A | 7/1963 | Oster |
| 3,427,161 | A | 2/1969 | Laridon et al. |
| 3,479,185 | A | 11/1969 | Chambers, Jr. |
| 3,549,367 | A | 12/1970 | Chang et al. |
| 4,343,885 | A | 8/1982 | Reardon, Jr. |
| 6,187,504 | B1 * | 2/2001 | Suwa ............ G03F 7/0045 430/270.1 |
| 7,776,510 | B2 * | 8/2010 | Iwai ............ C07C 309/04 430/270.1 |
| 8,431,325 | B2 | 4/2013 | Hashimoto et al. |

(Continued)

FOREIGN PATENT DOCUMENTS

| | | |
|---|---|---|
| CN | 103288796 A | 9/2013 |
| EP | 1260864 A1 | 11/2002 |

(Continued)

*Primary Examiner* — John S Chu
(74) *Attorney, Agent, or Firm* — Cantor Colburn LLP (57) ABSTRACT

A photoacid-generating compound has the structure

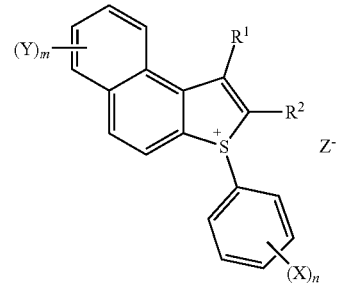

wherein m, n, $R^1$, $R^2$, X, Y, and $Z^-$ are defined herein. The photoacid-generating compound exhibits strong absorption and chemical sensitivity to extreme ultraviolet radiation, while also absorbing longer wavelengths with desirably reduced chemical sensitivity. Also described are a polymer incorporating the residue of a polymerizable version of the photoacid-generating compound, a photoresist composition that includes the photoacid-generating compound, the polymer, or a combination thereof, and a method of forming a photoresist relief image using the photoresist composition.

11 Claims, 4 Drawing Sheets

(56) References Cited

U.S. PATENT DOCUMENTS

| | | |
|---|---|---|
| 2001/0033990 A1 | 10/2001 | Hatakeyama et al. |
| 2002/0007716 A1 | 1/2002 | Shulman |
| 2003/0165776 A1 | 9/2003 | Yasunami et al. |
| 2004/0229162 A1 | 11/2004 | Ohsawa et al. |
| 2005/0026047 A1 | 2/2005 | Yang |
| 2008/0248422 A1 | 10/2008 | Iwai et al. |
| 2008/0311522 A1 | 12/2008 | Iwai et al. |
| 2010/0034294 A1 | 2/2010 | Jang et al. |
| 2010/0248149 A1 | 9/2010 | Tsuchimura et al. |
| 2010/0273105 A1 | 11/2010 | Utsumi et al. |
| 2010/0304296 A1 | 12/2010 | Ichikawa et al. |
| 2010/0316951 A1 | 12/2010 | Ichikawa et al. |
| 2011/0014568 A1 | 1/2011 | Ichikawa et al. |
| 2012/0251948 A1 | 10/2012 | Iizuka et al. |

FOREIGN PATENT DOCUMENTS

| | | |
|---|---|---|
| EP | 1353225 A2 | 10/2003 |
| JP | 2008033016 A | 2/2008 |
| JP | 2009069381 A | 4/2009 |
| JP | 2012083385 A | 4/2012 |
| WO | 2008013030 A1 | 1/2008 |

\* cited by examiner

PHOTOACID-GENERATING COMPOUND AND ASSOCIATED POLYMER, PHOTORESIST COMPOSITION, AND METHOD OF FORMING A PHOTORESIST RELIEF IMAGE

FIELD

The present invention relates to a photoacid-generating compound useful in photoresists compositions for microlithography.

INTRODUCTION

Extreme ultraviolet (EUV) photolithography utilizes radiation at 13.5 nanometer wavelength to create high-resolution features via chemical reactions in a photoresist layer. However, the EUV light source is typically also includes light at higher wavelengths, such as 193 and 248 nanometers. These contaminating wavelengths, sometimes called out-of-band (OOB) radiation, can be absorbed by the photoresist film and cause unwanted chemical changes that degrade image resolution.

There is therefore a desire for photoresist components, particularly photoacid generators, that are good absorbers of 13.5 nanometer radiation and are chemically sensitive to 13.5 nanometer radiation, while also absorbing OOB radiation and minimizing accompanying chemical sensitivity.

SUMMARY

One embodiment is a photoacid-generating compound having the structure wherein m is 0, 1, 2, 3, 4, 5, or 6; n is 0, 1, 2, 3, 4, or 5; $R^1$ and $R^2$ are each independently hydrogen, halogen, hydroxyl, carboxyl (—$CO_2H$), unsubstituted or substituted $C_{1-12}$ alkyl, unsubstituted or substituted $C_{1-12}$ alkoxyl, unsubstituted or substituted $C_{2-12}$ alkanoyl, unsubstituted or substituted $C_{2-12}$ alkanoyloxy, unsubstituted or substituted $C_{2-12}$ alkoxycarbonyl, unsubstituted or substituted $C_{3-12}$ anhydride, unsubstituted or substituted $C_{4-12}$ lactone, unsubstituted or substituted $C_{4-18}$ acetal, unsubstituted or substituted $C_{5-18}$ ketal, unsubstituted or substituted $C_{6-12}$ aryl provided that $R^1$ and $R^2$ are not linked to form a cycloaryl group; X and Y are independently at each occurrence halogen, hydroxyl, amino, thiol, carboxyl, amide, cyano, nitro, unsubstituted or substituted $C_{1-18}$ alkyl, unsubstituted or substituted $C_{1-18}$ alkoxyl, unsubstituted or substituted $C_{6-18}$ aryl, unsubstituted or substituted $C_{6-18}$ aryloxyl, unsubstituted or substituted $C_{7-18}$ alkylaryl, unsubstituted or substituted $C_{7-18}$ alkylaryloxyl, unsubstituted or substituted $C_{2-12}$ alkoxycarbonyl, unsubstituted or substituted $C_{4-18}$ acetal, or unsubstituted or substituted $C_{5-18}$ ketal; and $Z^-$ is an anion comprising a sulfonate group, a sulfonamidate group, a sulfonimidate group, a methide group, or a borate group; wherein Z optionally comprises a polymerizable group selected from vinyl, and an acryloyl group of the form —C(O)C($R^{11}$)=$CH_2$, wherein $R^{11}$ is hydrogen, fluoro, cyano, $C_{1-9}$ alkyl, or $C_{1-9}$ fluoroalkyl; provided that the photoacid-generating compound comprises at most one polymerizable group.

Another embodiment is a polymer comprising repeat units derived from a polymerizable photoacid-generating compound of the invention.

Another embodiment is a photoresist composition comprising the photoacid-generating compound, the polymer comprising repeat units derived from the polymerizable photoacid-generating compound, or a combination thereof.

Another embodiment is a method of forming a photoresist relief image, comprising: (a) applying a layer of the photoresist composition on a substrate to form a photoresist layer; (b) pattern-wise exposing the photoresist layer to activating radiation to form an exposed photoresist layer; and (c) developing the exposed photoresist layer to provide a photoresist relief image.

These and other embodiments are described in detail below.

DETAILED DESCRIPTION

The present inventor has determined that a photoacid-generating compound having a particular naphthothiophenium structure exhibits good absorption of and chemical sensitivity to extreme ultraviolet radiation, while also exhibiting significant absorption of but low chemical sensitivity to longer wavelength out-of-band radiation.

One embodiment is a photoacid-generating compound having the structure wherein m is 0, 1, 2, 3, 4, 5, or 6; n is 0, 1, 2, 3, 4, or 5; $R^1$ and $R^2$ are each independently hydrogen, halogen, hydroxyl, carboxyl (—$CO_2H$), unsubstituted or substituted $C_{1-12}$ alkyl, unsubstituted or substituted $C_{1-12}$ alkoxyl, unsubstituted or substituted $C_{2-12}$ alkanoyl, unsubstituted or substituted $C_{2-12}$ alkanoyloxy, unsubstituted or substituted $C_{2-12}$ alkoxycarbonyl, unsubstituted or substituted $C_{3-12}$ anhydride, unsubstituted or substituted $C_{4-12}$ lactone, unsubstituted or substituted $C_{4-18}$ acetal, unsubstituted or substituted $C_{5-18}$ ketal, unsubstituted or substituted $C_{6-12}$ aryl provided that $R^1$ and $R^2$ are not linked to form a cycloaryl group; X and Y are independently at each occurrence halogen, hydroxyl, amino, thiol, carboxyl, amide, cyano, nitro, unsubstituted or substituted $C_{1-18}$ alkyl, unsubstituted or substituted $C_{1-18}$ alkoxyl, unsubstituted or substituted $C_{6-18}$ aryl, unsubstituted or substituted $C_{6-18}$ aryloxyl, unsubstituted or substituted $C_{7-18}$ alkylaryl, unsubstituted or substituted $C_{7-18}$ alkylaryloxyl, unsubstituted or substituted $C_{2-12}$ alkoxycarbonyl, unsubstituted or substituted $C_{4-18}$ acetal, or unsubstituted or substituted $C_{5-18}$ ketal; and $Z^-$ is an anion comprising a sulfonate group, a sulfonamidate group, a sulfonimidate group, a methide group, or a borate group; wherein $Z^-$ optionally comprises a polymerizable group selected from vinyl, and an acryloyl group of the form $—C(O)C(R^{11})=CH_2$, wherein $R^{11}$ is hydrogen, fluoro, cyano, $C_{1-9}$ alkyl, or $C_{1-9}$ fluoroalkyl; provided that the photoacid-generating compound comprises at most one polymerizable group.

As used herein, "substituted" means including at least one substituent such as a halogen (i.e., F, Cl, Br, I), hydroxyl, amino, thiol, carboxyl, carboxylate, amide, cyano, sulfide, disulfide, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl. "Substituted" further means including at least one heteroatom within the carbon framework (as contrasted with pendant to the carbon framework). It will be understood that any group or structure disclosed with respect to the formulas herein may be so substituted unless otherwise specified. "Alkyl" includes linear, branched, cyclic, and polycyclic alkyl, and alkyl groups having a combination of at least two types of linear, branched, cyclic, and polycyclic alkyl fragments. "Fluorinated" means having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as $—CF_3$, $—C_2F_5$, $—C_3F_7$, or $—C_4F_9$). It will be understood that carbon counts for substituted groups include any carbon atoms of substituents. For example, the $C_{1-8}$-alkylene group in "substituted $—C(=O)—(C_{1-8}$-alkylene)-$C(=O)—$" has 1 to 8 carbon atoms, including any carbon atoms derived from substitution.

As used herein, the term "hydrocarbyl", whether used by itself, or as a prefix, suffix, or fragment of another term, refers to a residue that contains only carbon and hydrogen unless otherwise specified. The hydrocarbyl residue can be aliphatic or aromatic, straight-chain, cyclic, bicyclic, polycyclic, or branched, saturated or unsaturated. It can also contain combinations of aliphatic, aromatic, straight chain, cyclic, bicyclic, polycyclic, and branched groups, as well as saturated and unsaturated hydrocarbon moieties. When the hydrocarbyl residue is described as substituted, it can contain heteroatoms in addition to carbon and hydrogen.

In the structure of the photoacid-generating compound, m is a counter for the number of Y groups attached to the naphtho ring. Most broadly, m is 0, 1, 2, 3, 4, 5, or 6. In some embodiments, m is 0, 1, 2, or 3; or 0, 1, or 2; or 0 or 1; or 0. In some embodiments, m is 0.

In the structure of the photoacid-generating compound, m is a counter for the number of X groups attached to the phenyl group. Most broadly, n is 0, 1, 2, 3, 4, or 5. In some embodiments, n is 1, 2, 3, or 4; or 2, 3, or 4; or 2 or 3; or 3.

In the structure of the photoacid-generating compound, $R^1$ and $R^2$ are required substituents on the thiophenium nucleus. $R^1$ and $R^2$ are each independently hydrogen, halogen, hydroxyl, carboxyl ($—CO_2H$), unsubstituted or substituted $C_{1-12}$ alkyl (including $C_{1-12}$ halogenated alkyl, $C_{1-12}$ hydroxyalkyl, $C_{1-12}$ fluorinated hydroxyalkyl, and $C_{1-12}$ alkyl comprising an acryloyl group of the form $—C(O)C(R^{11})=CH_2$, wherein $R^{11}$ is hydrogen, fluoro, cyano, $C_{1-9}$ alkyl, or $C_{1-9}$ fluoroalkyl), unsubstituted or substituted $C_{1-12}$ alkoxyl (including methoxyl), unsubstituted or substituted $C_{2-12}$ alkanoyl (including acetyl), unsubstituted or substituted $C_{2-12}$ alkanoyloxy ($—OC(O)R^3$, wherein $R^3$ is unsubstituted or substituted $C_{HI}$ alkyl (including fluorinated alkyl)), unsubstituted or substituted $C_{2-18}$ alkoxycarbonyl ($—C(O)OR^3$, wherein $R^3$ is unsubstituted or substituted $C_{1-11}$ alkyl, including fluorinated alkyl; and $—C(O)OR^3$ can further include tertiary esters, $—C(O)OC(R^5)(R^6)(R^7)$, wherein $R^5$, $R^6$, and $R^7$ are each independently an unsubstituted or substituted $C_{1-14}$ hydrocarbyl provided the total number of carbon atoms in $R^5$, $R^6$, and $R^7$ does not exceed 16), unsubstituted or substituted $C_{3-12}$ anhydride ($—C(O)OC(O)R^4$, wherein $R^4$ is an unsubstituted or substituted $C_{1-10}$ alkyl), unsubstituted or substituted $C_{4-12}$ lactone, unsubstituted or substituted $C_{4-18}$ acetal ($L^1CH(OR^8)(OR^9)$, wherein $L^1$ is an unsubstituted or substituted $C_{1-10}$ alkylene, and $R^8$ and $R^9$ are each independently an unsubstituted or substituted $C_{1-10}$ alkyl provided that the total number of carbon atoms in $L^1$, $R^8$, and $R^9$ does not exceed 17), unsubstituted or substituted $C_{5-18}$ ketal)($L^1C(R^{10}$ ($OR^8$) ($OR^9$), wherein $L^1$ is an unsubstituted or substituted $C_{1-10}$ alkylene, and $R^8$ and $R^9$ are each independently an unsubstituted or substituted $C_{1-10}$ alkyl, and $R^{10}$ is an unsubstituted or substituted $C_{1-10}$ alkyl, provided that the total number of carbon atoms in $L^1$, $R^8$, $R^9$, and $R^{10}$ does not exceed 17), unsubstituted or substituted $C_{6-12}$ aryl (including phenyl, 3-vinylphenyl, 4-vinylphenyl, naphthyl), provided that $R^1$ and $R^2$ are not linked to form a cycloaryl group. In some embodiments, $R^1$ and $R^2$ are each independently hydrogen, $C_{1-12}$ alkyl, or $C_{2-12}$ alkoxycarbonyl ($—C(O)OR^3$, wherein $R^3$ is unsubstituted or substituted $C_{1-11}$ alkyl).

As noted above, X and Y are substituents on the phenyl group and naphtho group, respectively, of the photoacid-generating compound. X and Y are independently at each occurrence halogen, hydroxyl, amino, thiol, carboxyl ($—CO_2H$), amide ($—C(O)NH_2$), cyano, nitro, unsubstituted or substituted $C_{1-18}$ alkyl (including $C_{1-18}$ alkyl comprising an acryloyl group of the form $—C(O)C(R^{11})=CH_2$, wherein $R^{11}$ is hydrogen, fluoro, cyano, $C_{1-9}$ alkyl, or $C_{1-9}$ fluoroalkyl), unsubstituted or substituted $C_{1-18}$ alkoxyl, unsubstituted or substituted $C_{6-18}$ aryl (including phenyl, 3-vinylphenyl, 4-vinylphenyl, naphthyl), unsubstituted or substituted $C_{6-18}$ aryloxyl, unsubstituted or substituted $C_{7-18}$ alkylaryl, unsubstituted or substituted $C_{7-18}$ alkylaryloxyl, unsubstituted or substituted $C_{2-12}$ alkoxycarbonyl ($—C(O)OR^3$, wherein $R^3$ is unsubstituted or substituted $C_{1-11}$ alkyl, including fluorinated alkyl; and $—C(O)OR^3$ can further include tertiary esters, $—C(O)OC(R^5)(R^6)(R^7)$, wherein $R^5$, $R^6$, and $R^7$ are each independently an unsubstituted or substituted $C_{1-14}$ hydrocarbyl provided the total number of carbon atoms in $R^5$, $R^6$, and $R^7$ does not exceed 16), unsubstituted or substituted $C_{4-18}$ acetal ($L^1CH(OR^8)(OR^9)$, wherein $L^1$ is an unsubstituted or substituted $C_{1-10}$ alkylene, and $R^8$ and $R^9$ are each independently an unsubstituted or substituted $C_{1-10}$ alkyl provided that the total number of carbon atoms in $L^1$, $R^8$, and $R^9$ does not exceed 17), or unsubstituted or substituted $C_{5-18}$ ketal)($L^1C(R^{10}$ ($OR^8$) ($OR^9$), wherein $L^1$ is an unsubstituted or substituted $C_{1-10}$ alkylene, and $R^8$ and $R^9$ are each independently an unsubstituted or substituted $C_{1-10}$ alkyl, and $R^{10}$ is an unsubstituted or substituted $C_{1-10}$ alkyl, provided that the total number of carbon atoms in $L^1$, $R^8$, $R^9$, and $R^{10}$ does not exceed 17).

In some embodiments, n is 1, 2, or 3; and X is independently at each occurrence $C_{1-18}$ alkyl or $C_{2-12}$ alkoxycarbonyl (—C(O)$OR^3$, wherein $R^3$ is unsubstituted or substituted $C_{1-11}$ alkyl; in some embodiments, n is 1, 2, or 3, and at least one occurrence of X is tertiary-alkoxycarbonyl).

In the structure of the photoacid-generating compound, Z is an anion that balances the positive charge of the naphthothiophenium ion. Z can derive its negative charge from a sulfonate group (—$SO_3^-$), a sulfonamidate group (anion of sulfonamide; —S(O)$_2$N$^-$R$^a$, wherein R$^a$ is H or unsubstituted or substituted $C_{1-12}$ hydrocarbyl), a sulfonimidate group (anion of sulfonimide; —S(O)$_2$N$^-$S(O)$_2$R$^a$, wherein R$^a$ is H or unsubstituted or substituted $C_{1-12}$ hydrocarbyl), a methide group (including those in which the negatively charged carbon atom is directly bonded to at least two electron withdrawing groups), or a borate group. In some embodiments, Z comprises a polymerizable group selected from vinyl, and an acryloyl group of the form —C(O)C($R^{11}$)=$CH_2$, wherein $R^{11}$ is hydrogen, fluoro, cyano, $C_{1-9}$ alkyl, or $C_{1-9}$ fluoroalkyl.

Illustrative examples of $Z^-$ include
$CF_3SO_3^-$, $CF_3CF_2SO_3^-$, $CF_3(CF_2)_2SO_3^-$, $CF_3(CF_2)_3SO_3^-$, $CF_3(CF_2)_4SO_3^-$, $F_4B^-$, and $Ph_4B^-$.

The photoacid-generating compound comprises at most one polymerizable group. In other words, it comprises zero or one polymerizable group.

In some embodiments, the photoacid-generating compound has the structure wherein q is 0, 1, or 2; $R^{1a}$ and $R^{2a}$ are each independently $C_{1-12}$ alkyl; $R^5$, $R^6$, and $R^7$ are each independently an unsubstituted or substituted $C_{1-14}$ hydrocarbyl, wherein two of $R^5$, $R^6$, and $R^7$ can be connected to form a cyclic structure; and wherein the total number of carbon atoms in $R^5$, $R^6$, and $R^7$ does not exceed 16; $X^1$ is independently at each occurrence $C_{1-12}$ alkyl, or $C_{2-12}$ alkoxy carbonyl (—C(O)OR$^3$, wherein $R^3$ is unsubstituted or substituted $C_{1-11}$ alkyl); and Z is an anion comprising a sulfonate group, a sulfonamidate group, a sulfonimidate group, a methide group, or a borate group.

In some embodiments, the photoacid-generating compound includes an acid-labile group and has the structure -continued

, wherein Z⁻ is an anion comprising a sulfonate group, a sulfonamidate group, a sulfonimidate group, a methide group, or a borate group.

In some embodiments, the photoacid-generating compound includes a base-ionizable or base-labile group and has the structure , or wherein Z⁻ is an anion comprising a sulfonate group, a sulfonamidate group, a sulfonimidate group, a methide group, or a borate group.

In some embodiments, the photoacid-generating compound has the structure wherein q is 0, 1, 2, or 3; $X^1$ is independently at each occurrence an unsubstituted or substituted $C_{1-18}$ alkyl (including $C_{1-18}$ alkyl groups comprising a tertiary ester group, an acetal group, or a ketal group); and Z is an anion comprising a sulfonate group, a sulfonamidate group, a sulfonimidate group, a methide group, or a borate group.

The photoacid-generating compound can be polymerizable. For example, in some embodiments of the photoacid-generating compound, one of $R^1$ or $R^2$ or $Z^-$, or one occurrence of X, or one occurrence of Y, is a polymerizable group, provided that if one occurrence of X is the polymerizable group, then n is 1, 2, or 3, and provided that if one occurrence of Y is the polymerizable group, then m is 1, 2, or 3. When the polymerizable group is part of $R^1$, $R^2$, X, or Y, then polymerization of the photoacid-generating compound yields a polymer-bound cation. Alternatively, when the polymerizable group is part of $Z^-$, then polymerization of the photoacid-generating compound yields a polymer-bound anion. In some embodiments of the polymerizable photoacid-generating compound, it the structure wherein $R^{1a}$ and $R^{2a}$ are each independently unsubstituted or substituted $C_{1-12}$ alkyl, $C_{4-12}$ lactone, $C_{5-18}$ tertiary ester, $C_{4-18}$ acetal, or $C_{5-18}$ ketal; $R^{11}$ is hydrogen, fluoro, cyano, $C_{1-9}$ alkyl, or $C_{1-9}$ fluoroalkyl; and $Z^-$ is an anion comprising a sulfonate group, a sulfonamidate group, a sulfonimidate group, a methide group, or a borate group.

Another embodiment is a polymer comprising repeat units derived from the polymerizable photoacid-generating compound in any of its above-described variations. In addition to repeat units derived from the photoacid-generating compound comprising a polymerizable group, the polymer can, optionally, further comprise one or more of acid-labile monomers (including monomer comprising tertiary ester groups, acetal groups, and/or ketal groups), base-labile monomers (including monomers comprising lactone groups), and base-ionizable monomers (including monomers comprising 1,1,1,3,3,3-hexafluoro-2-hydroxy-2-propyl groups, —$NHSO_2CH_3$ groups, and —$NHSO_2CF_3$ groups).

Another embodiment is a photoresist composition comprising the photoacid-generating compound in any of its above-described variations, the polymer comprising repeat units derived from the polymerizable photoacid-generating compound in any of its above-described variations, or a combination of the photoacid-generating compound and the polymer.

In addition to the photoacid-generating compound or a polymer comprising the residue of the polymerizable photoacid-generating compound, the photoresist composition can further comprise one or more additional components, such as photoinitiators, surfactants, bases, solvents, and combinations thereof.

Photoinitiators are used in the photoresist composition for initiating polymerization of the cross-linking agents by generation of free-radicals. Suitable free radical photoinitiators include, for example, azo compounds, sulfur containing compounds, metallic salts and complexes, oximes, amines, polynuclear compounds, organic carbonyl compounds and mixtures thereof as described in U.S. Pat. No. 4,343,885, column 13, line 26 to column 17, line 18; and 9,10-anthraquinone; 1-chloroanthraquinone; 2-chloroanthraquinone; 2-methylanthraquinone; 2-ethylanthraquinone; 2-tert-butylanthraquinone; octamethylanthraquinone; 1,4-naphthoquinone; 9,10-phenanthrenequinone; 1,2-benzanthraquinone; 2,3-benzanthraquinone; 2-methyl-1,4-naphthoquinone; 2,3-dichloronaphthoquinone; 1,4-dimethylanthraquinone; 2,3-dimethylanthraquinone; 2-phenylanthraquinone; 2,3-diphenylanthraquinone; 3-chloro-2-methylanthraquinone; retenequinone; 7,8,9,10-tetrahydronaphthalenequinone; and 1,2,3,4-tetrahydrobenz(a)anthracene-7,12-dione. Other photoinitiators are described in U.S. Pat. No. 2,760,863 and include vicinal ketaldonyl alcohols, such as benzoin, pivaloin, acyloin ethers, e.g., benzoin methyl and ethyl ethers; and alpha-hydrocarbon-substituted aromatic acyloins, including alpha-methylbenzoin, alpha-allylbenzoin, and alpha-phenylbenzoin. Photoreducible dyes and reducing agents disclosed in U.S. Pat. Nos. 2,850,445; 2,875,047; and 3,097,096 as well as dyes of the phenazine, oxazine, and quinone classes; benzophenone, 2,4,5-triphenylimidazolyl dimers with hydrogen donors, and mixtures thereof as described in U.S. Pat. Nos. 3,427,161; 3,479,185; and 3,549,367 can be also used as photoinitiators.

Illustrative surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX™ PF-636, PF-6320, PF-656, and PF-6520 fluorosurfactants from Omnova.

Suitable bases include, for example, those based on hydroxides, carboxylates, amines, imines and amides. Such bases include $C_{1-30}$ organic amines, imines or amides, $C_{1-30}$ quaternary ammonium salts of strong bases (e.g., a hydroxide or alkoxide) or a weak base (e.g., a carboxylate). In some embodiments, the photoresist composition further comprises a base selected from the group consisting of $C_{1-30}$ amines, $C_{1-30}$ amides, and combinations thereof. Exemplary bases include amines such as Troger's base; hindered amines such as diazabicycloundecene (DBU), diazabicyclononene (DBN), and tetrahydroxy isopropyl diamine and tert-butyl-4-hydroxy-1-piperidiene carboxylate; ionic bases including quaternary alkyl ammonium salts such as tetrabutylammonium hydroxide (TBAH), tetramethylammonium 2-hydroxybenzoic acid (TMA OHBA), and tetrabutylammonium lactate. Suitable bases are further described in U.S. Pat. No. 8,431,325 to Hashimoto et al.

The photoresist composition components are typically dissolved in a solvent for dispensing and coating. Exemplary solvents include anisole; alcohols including 1-methoxy-2-propanol, and 1-ethoxy-2-propanol; esters including n-butyl acetate, ethyl lactate, 1-methoxy-2-propyl acetate, methoxyethoxy propionate, and ethoxyethoxy propionate; ketones including cyclohexanone and 2-heptanone; and combinations thereof. The solvent amount can be, for example, 70 to 99 weight percent, specifically 85 to 98 weight percent, based on the total weight of the photoresist composition.

Another embodiment is a method of forming a photoresist relief image, comprising: (a) applying a layer of the photoresist composition on a substrate to form a photoresist layer; (b) pattern-wise exposing the photoresist layer to activating radiation to form an exposed photoresist layer; and (c) developing the exposed photoresist layer to provide a photoresist relief image. The method can, optionally, further include (d) etching the resist relief pattern into the underlying substrate. In this embodiment, the photoresist composition can be the photoresist composition incorporating the photoacid-generating compound, or incorporating a polymer comprising a repeat unit derived from a polymerizable embodiment of the photoacid-generating compound. In some embodiments, the pattern-wise exposing comprises exposing with electron beam or extreme ultraviolet radiation.

The invention is further illustrated by the following non-limiting examples.

Example 1

Figure 1:
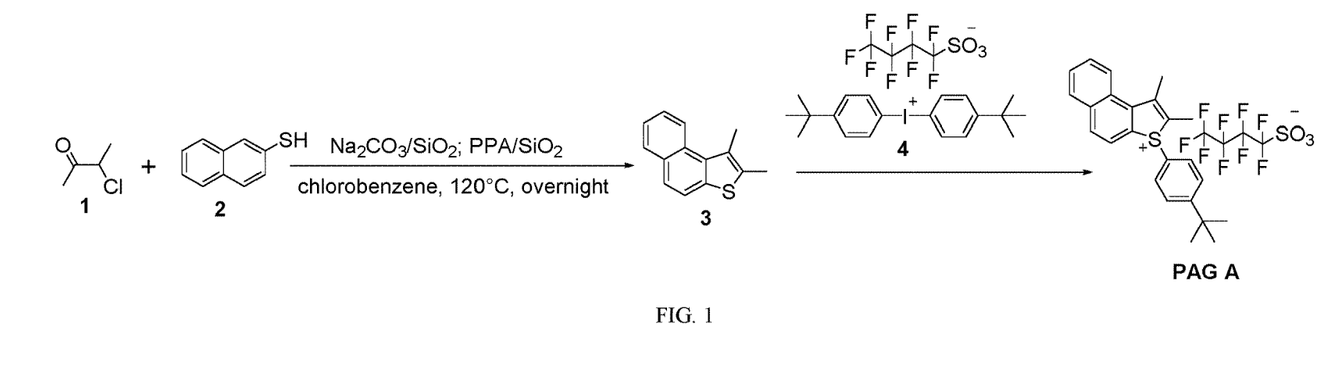
FIG. 1 is a synthetic scheme for synthesis of the photoacid-generating compound designated PAG A.

This example describes the synthesis of a photoacid-generating (PAG) compound designated PAG A. PAG A was synthesized in two steps as depicted in FIG. 1. The procedure for first step was adapted from the procedure reported by Aoyama et al., *Synthesis*, 2008, volume 13, pages 2089-2099. Thus, a mixture of 3-chlorobutan-2-one (1, 10.0 grams, 93.3 millimoles), naphthalene-2-thiol (2, 15.0 grams, 93.8 millimoles), 5.0 grams of silica gel supported sodium carbonate ($Na_2CO_3/SiO_2$, 1.0:5.3 weight/weight) and 5.0 grams of silica gel-supported polyphosphoric acid (PPA/$SiO_2$, 1:9 weight/weight) in 60 milliliters of chlorobenzene was stirred at 120° C. for 16 hours. The silica supported reagents were removed by filtration and the filtrate was evaporated to produce crude product 1,2-dimethylnaphtho[2,1-b]thiophene (3), which was purified by flash column chromatography using $CH_2Cl_2$ as a solvent. To the resulting $CH_2Cl_2$ solution was added 5.0 g of activated carbon and the mixture was stirred at room temperature for 15 minutes. The activated carbon was removed by filtration and the $CH_2Cl_2$ was completely removed under reduced pressure to produce the pure product 3. Yield 16.9 grams (85%). $^1$H NMR (acetone-$d_6$) δ: 2.60 (s, 3H), 2.78 (s, 3H), 7.55 (m, 2H), 7.77 (d, 1H), 7.87 (d, 1H), 8.05 (d, 1H), 8.75 (d, 1H).

In the second step PAG A was prepared as follows. A mixture of compound 3 (10.0 grams, 43.3 millimoles), di-t-butylphenyliodonium perfluorobutanesulfonate (salt 4, 32.6 grams, 47.0 millimoles) and 0.3 grams of cupric benzoate were suspended in 30 milliliters of chlorobenzene. The mixture was stirred and heated at reflux for 3.5 hours. The reaction mixture was cooled to room temperature and poured slowly into 100 milliliters of methyl t-butyl ether (MTBE). The resulting crude product was filtered off and dried. The crude product was dissolved in 100 milliliters of $CH_2Cl_2$ and treated with activated carbon. The solution was further washed with deionized water (5×100 milliliters) and the organic phase was concentrated to one-third the initial volume, poured into 300 milliliters methyl t-butyl ether, and the resulting pure PAG A was filtered and dried. Yield 15.0 grams (50%). $^1$H NMR (acetone-$d_6$) δ: 1.36 (s, 9H), 2.57 (s, 3H), 3.08 (s, 3H), 7.84 (m, 6H), 8.2 (m, 3H), 9.05 (s, 1H). $^{19}$F NMR (acetone-$d_6$) δ: −82.05 (s, 3F), −116.50 (s, 2F), −121.70 (s, 2F), −118.50 (s, 2F).

Example 2

Figure 2:
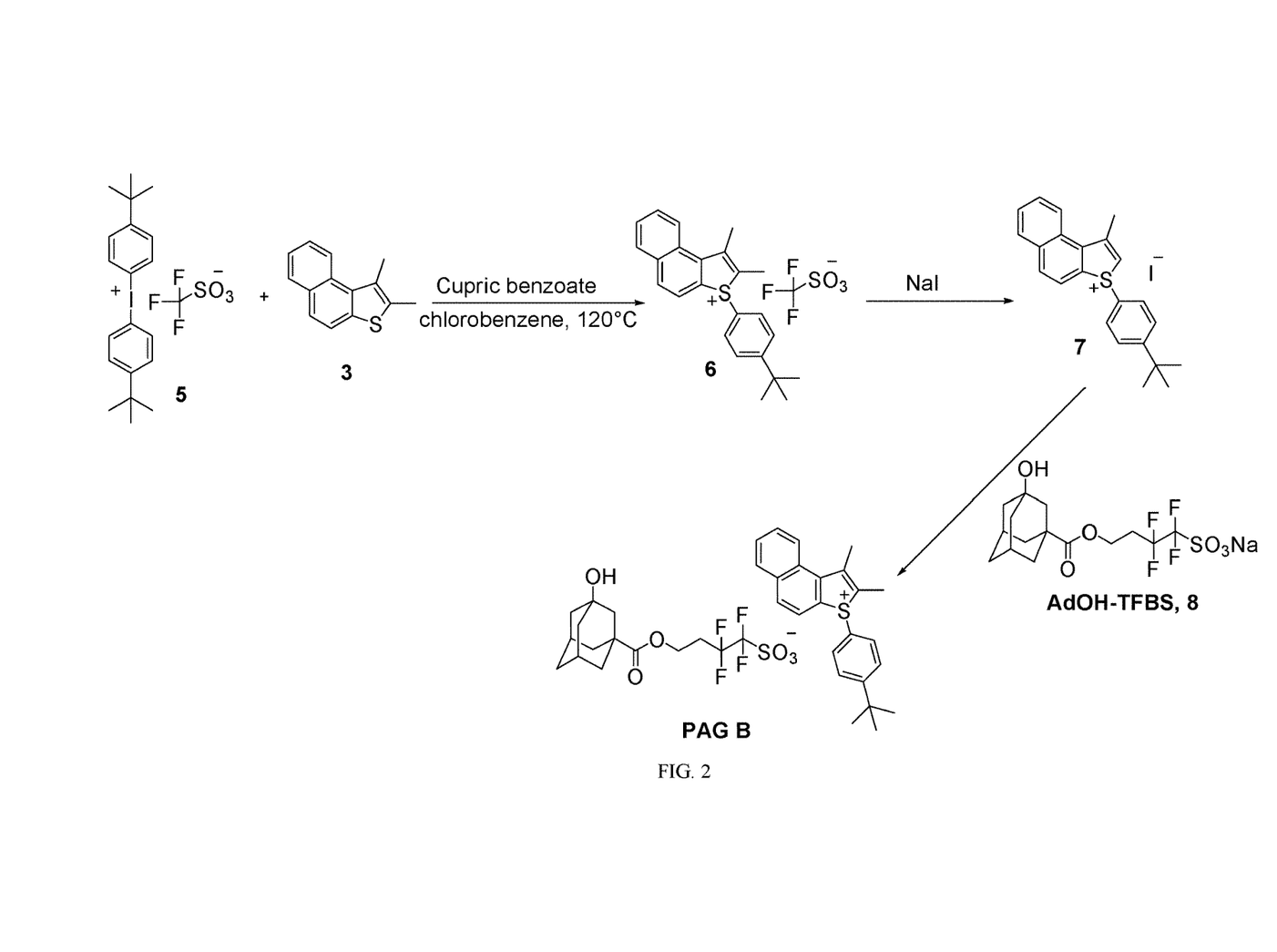
FIG. 2 is a synthetic scheme for synthesis of the photoacid-generating compound designated PAG B.

This example describes the synthesis of a photoacid-generating (PAG) compound designated PAG B. PAG B was synthesized in two steps as depicted in FIG. 2. A mixture of compound 3 (10.7 grams, 50.40 millimoles), bis(4-(tert-butyl)phenyl)iodonium trifluoromethanesulfonate (5, 25.0 grams, 46.1 millimoles) and 0.37 grams of cupric benzoate was suspended in 100 milliliters of chlorobenzene. The mixture was stirred and heated at reflux for 3 hours. The reaction mixture was cooled to room temperature, and poured slowly into 2.0 liters of methyl t-butyl ether. The resulting crude product was filtered off and dried. The crude product 6 was dissolved in 200 milliliters of $CH_2Cl_2$ and washed with a saturated aqueous solution of sodium iodide (8×50 milliliters). The organic phase was separated, the solvent volume reduced to 30 milliliters and the concentrated solution was poured slowly into 2.5 liters of methyl t-butyl ether to precipitate compound 7, which was filtered and dried. The amount of the crude product 7 was 18.6 grams. This product was used in the next step without further purification. Compound 7 (15.0 grams, 32.75 millimoles) and AdOH-TFBS (salt 8, 15.0 grams, 35.20 millimoles) were mixed in 100 milliliters water and 100 milliliters $CH_2Cl_2$ and the mixture was stirred at room temperature for 1 hour. The organic phase was washed with deionized water (5×100 mL) and then was concentrated to one-third the initial volume, poured into 1.0 liter methyl t-butyl ether and the resulting pure product PAG B was filtered and dried. Yield 23.4 grams (yield of the last ion exchange reaction was 85%). $^1$H NMR (acetone-$d_6$) δ: 1.36 (s, 9H), 1.79-1.53 (m, 12H), 2.18 (s, 2H), 2.57 (s, 3H), 2.70 (m, 2H), 3.08 (s, 3H), 4.35 (t, 2H), 7.84 (m, 6H), 8.2 (m, 3H), 9.05 (s, 1H). $^{19}$F NMR (acetone-$d_6$) δ: −119.15 (2F, $CF_2SO_3$), 112.67 (2F, $CH_2CF_2CF_2SO_3$). Positive liquid chromatography-mass spectrometry (LC-MS) traces indicate 98% purity of the cation, and negative LC-MS traces indicate 98% purity of the anion.

Example 3

Figure 3:
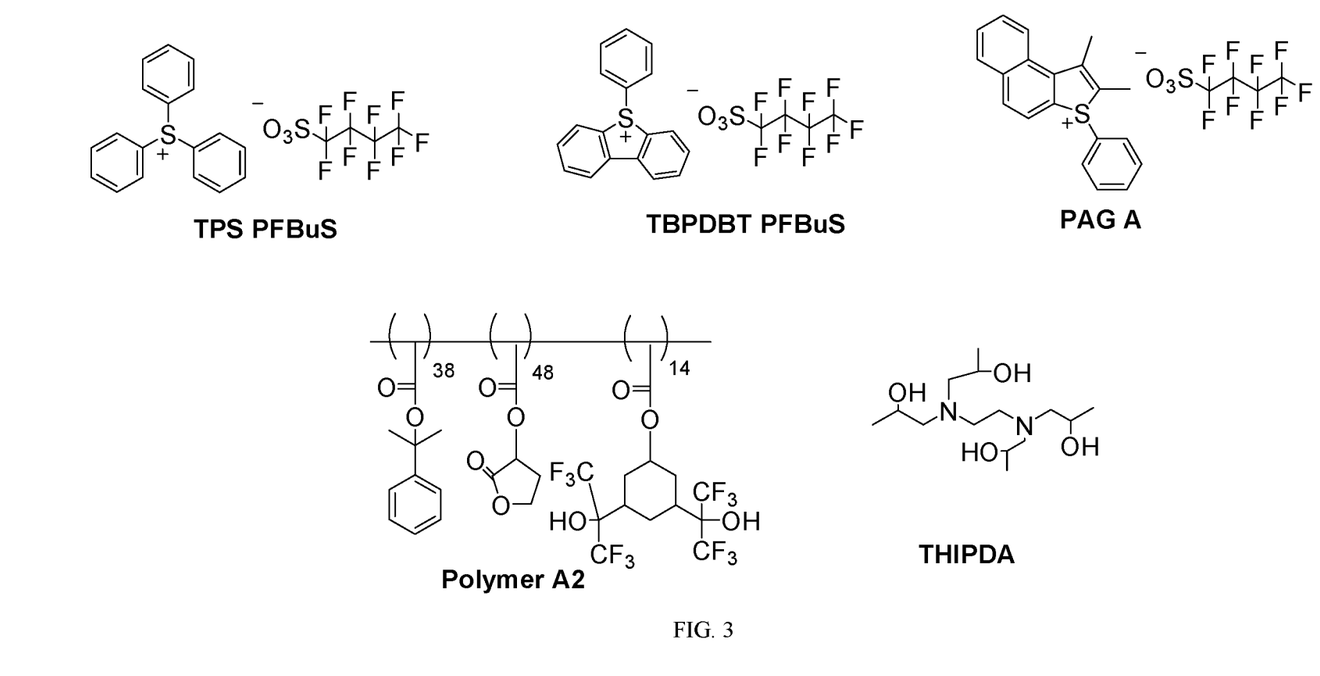
FIG. 3 shows the chemical structures of some components used in formulating the photoresist compositions of Example 3.

This example describes sensitivity measurements on photoresist compositions containing photoacid-generating compounds. Contrast curves measurements were performed for three photoresists. The structure of the photoacid generator compounds, polymer A2, and the base that were used in the formulations are shown in FIG. 3. The formulation components and proportions are summarized in Table 1, where "PAG wt %" is the weight percent of photoacid-generating compound, based on the total weight of solids; "Base wt % (THIPDA)" is the weight percent of N,N,N',N'-tetrakis(2-hydroxypropyl)ethylenediamine (THIPDA), based on the total weight of solids; "SLA wt %" is the weight percent of Surface Leveling Agent, also referred to as surfactant, obtained as POLYFOX™ PF-656, available from Omnova, based on the total weight of solids. The solvent used in these formulations was ethyl lactate. The final percent solids in all formulations was 2.5%.

TABLE 1

| Photoresist | Polymer | PAG | PAG wt % | Base (THIPDA) wt % | SLA wt % |
|---|---|---|---|---|---|
| A (comparative) | A2 | TPS PFBuS | 8.30 | 0.267 | 0.09 |
| B (comparative) | A2 | TBPDBT PFBuS | 9.11 | 0.267 | 0.09 |
| C | A2 | PAG A | 10.24 | 0.267 | 0.09 |

Each photoresist solution was coated onto a silicon wafer that had been pre-coated with a bottom anti-reflective coating (Rohm & Haas BARC AR9) using a TEL ATC8 coater. The photoresist coating had a target thickness of 60 nanometers. A post-application bake (PAB; also known as soft bake) was conducted at 130° C. for 90 seconds, and a post-exposure bake (PEB) was conducted at a temperature of 100° C. for 60 seconds. The wafers were exposed in a 10×10 $E_0$ array ArF tool (193 nm radiation). The wafers were then developed with 0.26 Normal aqueous tetramethylammonium hydroxide (TMAH), and $E_0$ values were extracted from the contrast curve of each wafer. Similar experiments were performed for an $E_0$ array using an EUV-ES 9000 LTJ tool (EUV radiation, 13.4 nm), and a Canon ES4 KrF tool (248 nm radiation). Table 2 summarizes the clearing doses ($E_0$) at 193 nm, 248 nm, and 13.4 nm radiation for three formulations that are similar except for the PAG additive. The Clearing Dose $E_0$ (mJ/cm$^2$) is defined as the amount of exposure energy required to clear the resist. $E_0$ is determined from the resist contrast curve, which is a plot of the film thickness of resist remaining after exposure and development, as a function of exposure energy. The exposure at which the film clears completely is the clearing dose, $E_0$, expressed in units of millijoules per square-centimeter. The $E_0$ results in Table 2 indicate slower photospeed or lower sensitivity for formulations that contain formulation C compared to the comparative formulations A and B. Furthermore, the ratio of 13.4 nm $E_0$/248 nm $E_0$ is the smallest for formulation C, indicating that PAG C possess the lowest sensitivity at 248 nm radiation. Similarly, the ratio of 13.4 nm $E_0$/193 nm $E_0$ is the smallest for formulation C, indicating that PAG C possess the lowest sensitivity at 193 nm radiation.

These results demonstrate that photoacid generator compound PAG A is less sensitive to deep-ultraviolet out-of-band radiation compared to comparative photoacid generator compounds TPS PFBuS and TBPDBT PFBuS.

Example 4

Figure 4:
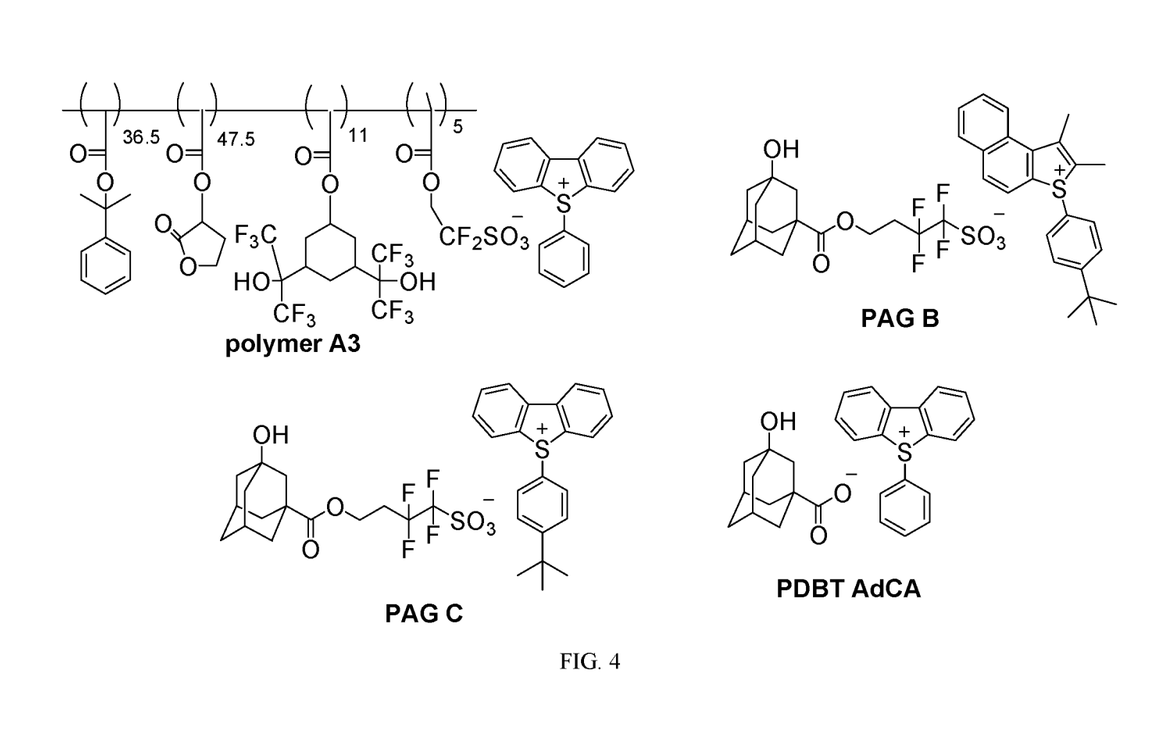
FIG. 4 shows the chemical structures of some components used in formulating the photoresist compositions of Example 4.

This example describes evaluation of photoresist compositions formulated for EUV exposure. Table 3 summarizes the components and proportions of photoresist E and comparative photoresist D. In Table 3, "PAG wt %" is the weight percent of photoacid-generating compound, based on the total weight of solids, "wt % PDBT AdCA" is the weight percent of PDBT AdCA, based on the total weight of solids, and "wt % THIPDA" is the weight percent of THIPDA, based on the total weight of solids. In addition to base THIPDA, PAG-containing polymer A3, PAG B, comparative PAG C, and the base PDBT AdCA were used in the two formulations (see FIG. 4 for structures). The percent solids for the two formulations was 2.5% and the solvent was a blend of ethyl lactate/methyl 2-hydroxyisobutyrate, 7:3 weight/weight. Lithographic evaluations at EUV wavelengths were obtained using the AMET tool at the SEMATECH facility in Albany, N.Y., USA. Each photoresist solution was coated onto a silicon wafer that had been pre-coated with an organic bottom anti-reflective coating, at a thickness of 25 nanometers. The photoresist coating had target thickness of 50 nanometers. Post-application bake was conducted at 110° C. for 90 seconds, and post-exposure bake was conducted at 100° C. for 60 seconds. Illumination conditions were: numerical aperture=0.30; Quad; 0.36σ/0.93σ; Photo-Mask; Subfield H/V; Cleave LS. Wafers were then developed with 0.26 Normal aqueous TMAH for 30 seconds.

TABLE 3

| Photoresist | Polymer | PAG | PAG wt % | wt % PDBT AdCA/wt % THIPDA |
|---|---|---|---|---|
| D (comparative) | A3 | PAG C | 19.514 | 1.19/0.3 |
| E | A3 | PAG B | 20.27 | 1.19/0.3 |

Photolithographic results are summarized in Table 4, where "$E_{size}$" is sizing energy expressed in units of millijoules per square-centimeter, "PCM" is pattern collapse margin expressed in units of nanometers, "LWR" is line width roughness expressed in units of nanometers, "Exposure Latitude" is expressed in units of percent and is defined as a difference in exposure energy to print +/−10% of the target diameter normalized by the sizing energy, and Focus Latitude (FL) is the range of focus that keeps the linewidth within 10% of the critical dimension (CD). The results in Table 4 show that Photoresist E, comprising the photoacid-generating compound of this invention, demonstrates resolution of features as small as 26 nanometer half pitch (hp) line/space at an acceptable photospeed, good pattern collapse margin and exposure latitude, as well as acceptable LWR. The inventive example also shows a clear focus latitude advantage.

TABLE 2

| Formulation | PAG | 248 nm $E_0$ (mJ/cm$^2$) | 193 nm $E_0$ (mJ/cm$^2$) | 13.4 nm $E_0$ (mJ/cm$^2$) | 13.4 nm $E_0$/248 nm $E_0$ | 13.4 nm $E_0$/248 nm $E_0$ |
|---|---|---|---|---|---|---|
| A (comparative) | TPS PFBuS | 7.5 | 2.5 | 2.5 | 0.330 | 1.00 |
| B (comparative) | TBPDBT PFBuS | 36.0 | 7.8 | 3.4 | 0.094 | 0.43 |
| C | PAG A | 45.0 | 8.6 | 3.5 | 0.077 | 0.40 |

TABLE 4

| | Photoresist D | Photoresist E |
|---|---|---|
| 26 nm Esize (mJ/cm$^2$) | 12.30 | 12.25 |
| FL (10% CD) (μm) | 0.130 | 0.244 |
| 26 nm EL (%) | 10.5 | 10.2 |
| PCM (nm) | 19.4 | 19.0 |
| Best LWR (nm) | <5.5 | <5.5 |

The invention claimed is:

1. A photoacid-generating compound having the structure wherein
m is 0, 1, 2, 3, 4, 5, or 6;
n is 0, 1, 2, 3, 4, or 5;
$R^1$ and $R^2$ are each independently hydrogen, halogen, hydroxyl, carboxyl (—CO$_2$H), unsubstituted or substituted $C_{1-12}$ alkyl, unsubstituted or substituted $C_{1-12}$ alkoxyl, unsubstituted or substituted $C_{2-12}$ alkanoyl, unsubstituted or substituted $C_{2-12}$ alkanoyloxy, unsubstituted or substituted $C_{2-12}$ alkoxycarbonyl, unsubstituted or substituted $C_{3-12}$ anhydride, unsubstituted or substituted $C_{4-12}$ lactone, unsubstituted or substituted $C_{4-18}$ acetal, unsubstituted or substituted $C_{5-18}$ ketal, unsubstituted or substituted $C_{6-12}$ aryl provided that $R^1$ and $R^2$ are not linked to form a cycloaryl group;
X and Y are independently at each occurrence halogen, hydroxyl, amino, thiol, carboxyl, amide, cyano, nitro, unsubstituted or substituted $C_{1-18}$ alkyl, unsubstituted or substituted $C_{1-18}$ alkoxyl, unsubstituted or substituted $C_{6-18}$ aryl, unsubstituted or substituted $C_{6-18}$ aryloxyl, unsubstituted or substituted $C_{7-18}$ alkylaryl, unsubstituted or substituted $C_{7-18}$ alkylaryloxyl, unsubstituted or substituted $C_{2-12}$ alkoxycarbonyl, unsubstituted or substituted $C_{4-18}$ acetal, or unsubstituted or substituted $C_{5-18}$ ketal; and
$Z^-$ is an anion comprising a sulfonate group, a sulfonamidate group, a sulfonimidate group, a methide group, or a borate group; wherein $Z^-$ optionally comprises a polymerizable group selected from vinyl, and an acryloyl group of the form —C(O)C($R^{11}$)=CH$_2$, wherein $R^{11}$ is hydrogen, fluoro, cyano, $C_{1-9}$ alkyl, or $C_{1-9}$ fluoroalkyl;
provided that the photoacid-generating compound comprises at most one polymerizable group.

2. The photoacid-generating compound of claim 1, wherein $R^1$ and $R^2$ are each independently hydrogen, $C_{1-12}$ alkyl, or $C_{2-12}$ alkoxycarbonyl.

3. The photoacid-generating compound of claim 1, wherein n is 1, 2, or 3; and X is independently at each occurrence $C_{1-18}$ alkyl or $C_{2-12}$ alkoxycarbonyl.

4. The photoacid-generating compound of claim 1, wherein m is zero.

5. The photoacid-generating compound of claim 1, having the structure wherein
q is 0, 1, or 2;
$R^{1a}$ and $R^{2a}$ are each independently $C_{1-12}$ alkyl;

R⁵, R⁶, and R⁷ are each independently an unsubstituted or substituted $C_{1-14}$ hydrocarbyl, wherein two of R⁵, R⁶, and R⁷ can be connected to form a cyclic structure; and wherein the total number of carbon atoms in R⁵, R⁶, and R⁷ does not exceed 16;

X¹ is independently at each occurrence $C_{1-12}$ alkyl, or $C_{2-12}$ alkoxy carbonyl; and Z⁻ is an anion comprising a sulfonate group, a sulfonamidate group, a sulfonimidate group, a methide group, or a borate group.

6. The photoacid-generating compound of claim 1, having the structure wherein
q is 0, 1, 2, or 3;
X¹ is independently at each occurrence an unsubstituted or substituted $C_{1-18}$ alkyl; and
Z⁻ is an anion comprising a sulfonate group, a sulfonamidate group, a sulfonimidate group, a methide group, or a borate group.

7. The photoacid-generating compound of claim 1, wherein one of R¹ or R² or Z⁻, or one occurrence of X, or one occurrence of Y, is a polymerizable group, provided that if one occurrence of X is the polymerizable group, then n is 1, 2, or 3, and provided that if one occurrence of Y is the polymerizable group, then m is 1, 2, or 3.

8. A polymer comprising repeat units derived from the photoacid-generating compound of claim 7.

9. A photoresist composition comprising the photoacid-generating compound of any one of claims 1 to 6.

10. A method of forming a photoresist relief image, comprising:
(a) applying a layer of the photoresist composition of claim 9 on a substrate to form a photoresist layer;
(b) pattern-wise exposing the photoresist layer to activating radiation to form an exposed photoresist layer; and
(c) developing the exposed photoresist layer to provide a photoresist relief image.

11. A photoresist composition comprising the polymer of claim 8.

* * * * *